United States Patent
Ruiz

[11] Patent Number: 6,117,097
[45] Date of Patent: Sep. 12, 2000

[54] ADJUSTABLE TENSION JOINT BRACE APPARATUS

[76] Inventor: Andres F. Ruiz, 7434 W. 30 Ave., Hialeah, Fla. 33018

[21] Appl. No.: 09/148,965

[22] Filed: Sep. 5, 1998

[51] Int. Cl.$^7$ .............................. A61F 5/00; A61F 13/00
[52] U.S. Cl. .............................. 602/26; 602/20; 602/23; 602/60; 602/62; 602/63
[58] Field of Search .............................. 602/4, 20, 21, 602/16, 23, 26, 60, 61, 62, 63; 482/111, 112, 118, 124, 127; 473/214, 276, 458; 601/33, 34

[56] References Cited

U.S. PATENT DOCUMENTS

| | | |
|---|---|---|
| 1,510,408 | 9/1924 | Lychou . |
| 3,698,389 | 10/1972 | Gnedel . |
| 4,220,148 | 9/1980 | Labnels . |
| 4,492,227 | 1/1985 | Senn et al. . |
| 4,832,010 | 5/1989 | Lerman ........................... 602/26 X |
| 4,875,677 | 10/1989 | Tetreault ........................... 473/458 |
| 4,899,735 | 2/1990 | Townsend . |
| 5,352,190 | 10/1994 | Fischer et al. . |
| 5,437,619 | 8/1995 | Malewicz et al. . |
| 5,472,410 | 12/1995 | Hammersly . |
| 5,807,298 | 9/1998 | Palumbo ........................... 602/62 |
| 5,857,988 | 1/1999 | Shirley ........................... 602/26 |
| 5,865,714 | 2/1999 | Marlowe ........................... 482/112 |
| 5,873,848 | 2/1999 | Fulkerson ........................... 602/62 |
| 5,891,079 | 4/1999 | Barnes ........................... 602/61 |
| 5,954,678 | 9/1999 | Cruz ........................... 602/26 |

Primary Examiner—Kim M. Lee
Attorney, Agent, or Firm—Frank L. Kubler

[57] ABSTRACT

A brace apparatus for applying tension to the fore portion and the upper portion of a human limb about a limb joint in a direction of limb closure about the joint for joint therapy includes a limb fore portion engaging structure; a limb upper portion engaging structure; an elastic strip interconnecting the limb fore portion and the limb upper portion for creating a range of tension levels between the limb fore portion and the limb upper portion over which the limb fore portion and the limb upper portion move relative to each other; and a mechanism for adjusting the range of tension in the elastic strip. The limb fore portion engaging structure and the limb upper portion engaging structure preferably include a flexible tubular member sized to fit about the human limb at the joint, the tubular member having a longitudinal slit for opening the member for placement of the member about the limb; and a tubular member fastener at the longitudinal slit releasibly fastening the slit against opening and thereby securing the member about the limb. The elastic strip is preferably connected to the member adjacent to the fore limb portion and to the member adjacent to the upper limb portion. The mechanism for adjusting the range of tension optionally includes a button secured to the strip and a longitudinal series of button holes in the member for receiving the button, so that the range of tension in the elastic member is selected by selecting a button hole for receiving the button.

7 Claims, 2 Drawing Sheets

ADJUSTABLE TENSION JOINT BRACE APPARATUS

BACKGROUND OF THE INVENTION

1. Field of the Invention

The present invention relates generally to the field of physical therapy aids and equipment. More specifically the present invention relates to a brace apparatus for applying selectable tension to a human joint such as a knee or an elbow, the tension pulling in the direction about which the limb closes around the joint. This tension serves either to progressively increase the range of joint movement or to provide resistance against which to exercise.

The apparatus includes a flexible tubular member sized to fit closely around a human limb and tension means in the form of an elastic strip connected to the member at either side of the joint. Tension selection means are provided for adjusting the magnitude of tension in the strip.

2. Description of the Prior Art

There have long been straps and other devices for supporting a human limb in a raised or angled position. One common example is the cast which holds a broken arm or leg in a bent position.

Malewicz, et al., U.S. Pat. No. 5,437,619, issued on Aug. 1, 1995, discloses a range-of-motion splint with an eccentric spring. Malewicz, et al., includes forearm collar, an upper arm collar, a first arm segment extending from adjacent the limb joint to engagement with the forearm collar and a second arm segment extending from adjacent the limb joint to engagement with the upper arm collar. A helical spring assembly pivotally interconnects the first and second arm segments and biases the arm segments and thus the nearer forearm and upper arm toward either an open position or a closed position. A key feature of Malewicz, et al., is that the helical spring is eccentrically mounted to give steady biasing throughout the arm range of movement at the joint. A problem with Malewicz, et al., is that the apparatus is relatively complex, heavy, costly and uncomfortable to wear.

Shirley, et al. U.S. Pat. No. 5,599,288, issued on Feb. 4, 1997, teaches an external ligament system. Shirley, et al., provides a brace for persons who have suffered damage to the ligaments of the knee for holding the tibia and the fibula against relative front to back motion while permitting the knee to bend. Shirley, et al. includes an elongated leg sheath and a pair of hinged external linkages. Each linkage is anchored to the sheath on one side of the leg, crosses over the leg and around a grooved roller on the opposing side and then crosses back again to the first side of the leg where it is anchored. A problem with Shirley, et al., is that it merely provides support, and offers no elastic tension as resistance to exercise against.

Fischer, et al., U.S. Pat. No. 5,352,190, issued on Oct. 4, 1994, reveals a knee brace. Fischer, et al., includes a first cuff fitted to the leg above the knee and a second cuff fitted to the leg below the knee, bendable linkages interconnecting the cuffs along the leg, and a hydraulic or pneumatic force applying mechanism extending between the cuffs. The force applying mechanism, which may be a hydraulic cylinder, either forces the knee into a bent position or into an unbent position, or bends and unbends the knee in a continuous cycle. Alternatively Fischer, et al., can be used to retain the knee in a fixed position to protect an injured joint. Problems with Fischer, et al., are that it is complex, heavy and expensive and does not, in its intended form, provide selectable resistance to joint movement for therapeutic exercise.

Tetreault, U.S. Pat. No. 4,875,677, issued on Oct. 24, 1989, discloses a lead arm strap for baseball hitters. The arm strap includes a first cuff which is fitted snugly around the forearm and a second cuff which is similarly fitted around the upper arm. Elastic straps joined at their ends to cuff buckles interconnect the cuffs along the inside of the arm, and bias the forearm and upper arm into a right angle relationship. Tetreault retains the arm in the proper hitting stance. A problem with Tetreault if used for physical therapy is that it produces tension only where the arm is extended beyond a ninety degree bend, and thus would produce incomplete exercise of the joint. Another problem is that no provision is made for changing the magnitude of tension resistance for progression in strength and arm flexibility and for different patients and conditions.

Other potentially relevant references are Lychou, U.S. Pat. No. 1,510,408, issued on Sep. 30, 1924 for a knee brace; Guedel, U.S. Pat. No. 3,698,389, issued on Oct. 17, 1972, for an elbow locking device; Labnels, U.S. Pat. No. 4,220,148, issued on Sep. 2, 1980 for a knee stabilizer; Senn, et al., U.S. Pat. No. 4,492,227, issued on Jan. 8, 1985, for an elastic knee bandage; Townsend, et al., U.S. Pat. No. 4,899,735, issued on Feb. 13, 1990 for a torsion bar splint for the forearm; and Hammersly, U.S. Pat. No. 5,472,410, issued on Dec. 5, 1995 for an adjustable flexion and extension joint orthoses.

It is thus an object of the present invention to provide a physical therapy limb brace apparatus which engages the limb on either side of a joint and which biases the joint toward a closed position.

It is another object of the present invention to provide such a brace apparatus which applies biasing tension which is readily adjustable to provide a progression of increased pull throughout treatment and to provide different tension ranges for different patients having differing conditions.

It is still another object of the present invention to provide such a brace apparatus which is easily fitted to and removed from a patient, and is light weight and comfortable.

It is finally an object of the present invention to provide such a brace apparatus which is simple in construction and is very inexpensive to manufacture.

SUMMARY OF THE INVENTION

The present invention accomplishes the above-stated objectives, as well as others, as may be determined by a fair reading and interpretation of the entire specification.

A brace apparatus is provided for applying tension to the fore portion and the upper portion of a human limb about a limb joint in a direction of limb closure about the joint for joint therapy, including a limb fore portion engaging structure; a limb upper portion engaging structure; an elastic strip interconnecting the limb fore portion and the limb upper portion for creating a range of tension levels between the limb fore portion and the limb upper portion over which the limb fore portion and the limb upper portion move relative to each other; and a mechanism for adjusting the range of tension in the elastic strip.

The limb fore portion engaging structure and the limb upper portion engaging structure preferably include a flexible tubular member sized to fit about the human limb at the joint, the tubular member having a longitudinal slit for opening the member for placement of the member about the limb; and a tubular member fastener at the longitudinal slit releasibly fastening the slit against opening and thereby securing the member about the limb. The elastic strip is preferably connected to the member adjacent to the fore limb portion and to the member adjacent to the upper limb portion.

The mechanism for adjusting the range of tension optionally includes a button secured to the strip and a longitudinal series of button holes in the member for receiving the button, so that the range of tension in the elastic member is selected by selecting a button hole for receiving the button. The mechanism for adjusting the range of tension alternatively includes a rivet connected to the member about which the elastic strip is removably wound to hold the strip at a selected elastic elongation. The tubular member preferably includes an opening positioned to expose the outside portion of the joint. The apparatus may include two or more of the elastic strips and one or more mechanisms for adjusting the range of tension in each of the two or more elastic strips.

BRIEF DESCRIPTION OF THE DRAWINGS

Various other objects, advantages, and features of the invention will become apparent to those skilled in the art from the following discussion taken in conjunction with the following drawings, in which.

DETAILED DESCRIPTION OF THE PREFERRED EMBODIMENTS

Figure 1:
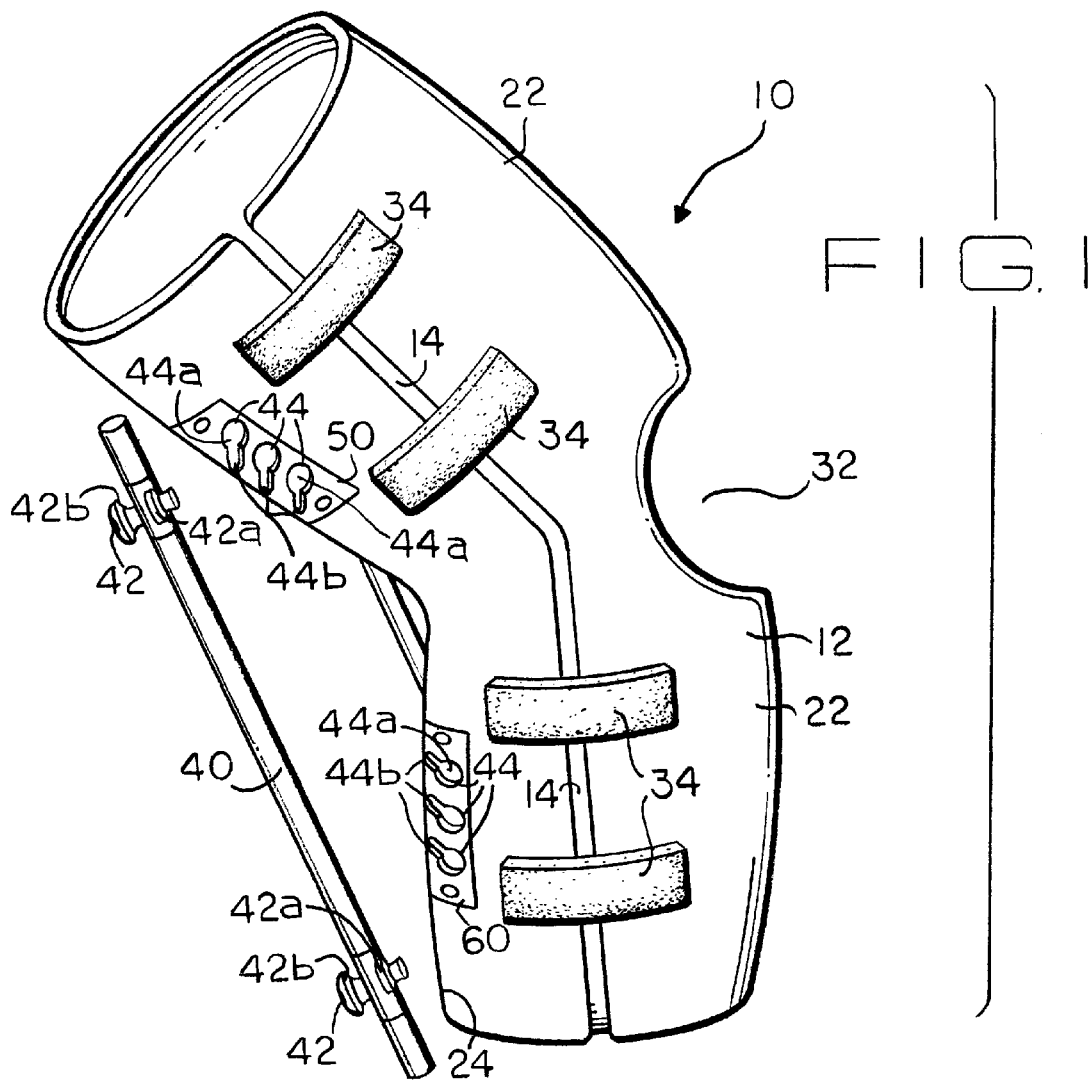
FIG. 1 is a perspective side view of the first embodiment of the brace invention, having the elastic buttons and tubular member button holes.

As required, detailed embodiments of the present invention are disclosed herein; however, it is to be understood that the disclosed embodiments are merely exemplary of the invention which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Reference is now made to the drawings, wherein like characteristics and features of the present invention shown in the various FIGURES are designated by the same reference numerals.

First Preferred Embodiment

Figure 2:
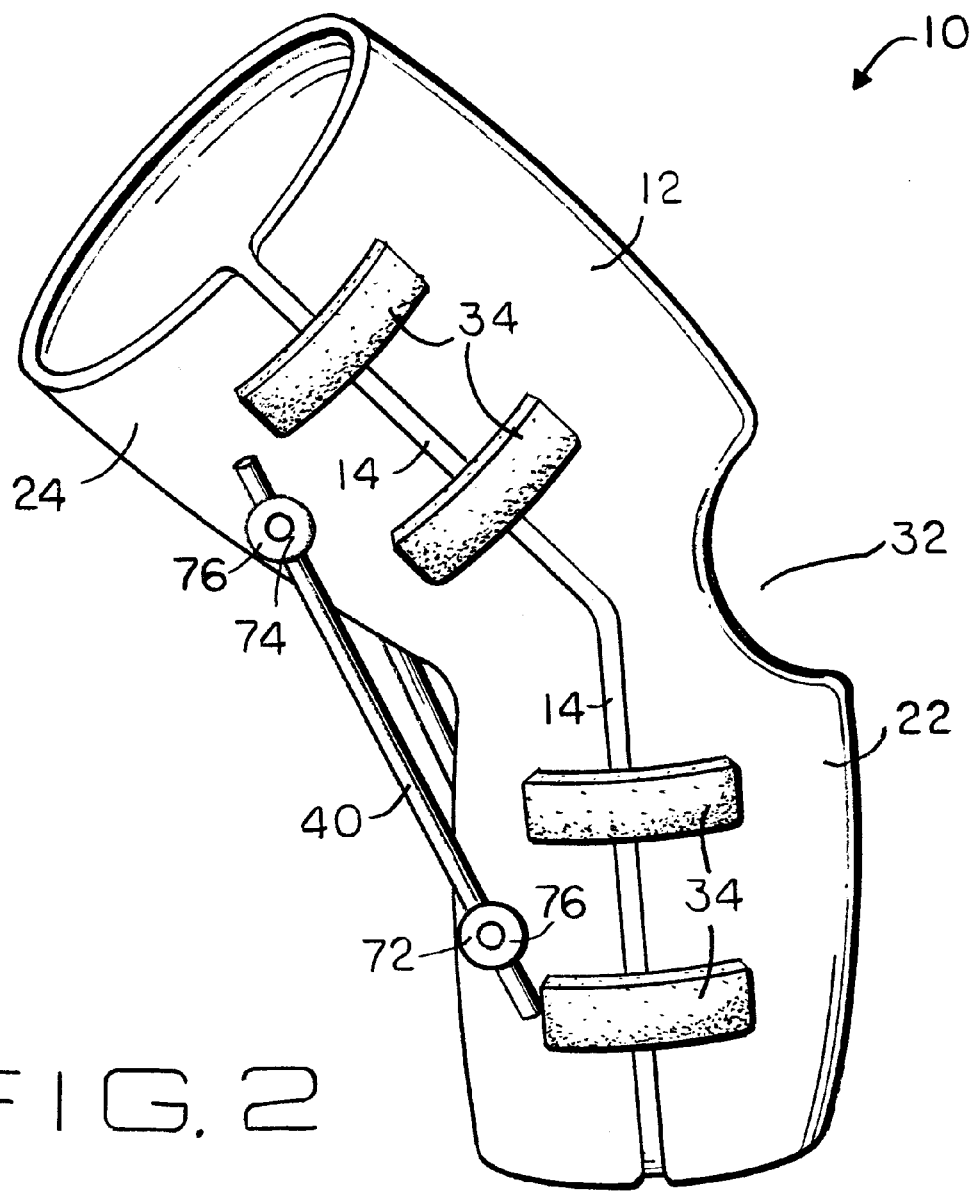
FIG. 2 is a perspective side view of the second embodiment of the brace invention, having the wide headed rivets in the tubular arm portion.

Referring to FIGS. 1–2, a brace apparatus 10 is disclosed for applying selectable tension to a human joint such as a knee or an elbow in the direction of limb closure about the joint. The a human joint is understood to have a limb fore portion such as the forearm and a limb upper portion such as an arm upper portion.

Apparatus 10 includes a flexible tubular member 12 sized to fit closely around a human limb such as a leg or an arm at the joint, and having a longitudinal slit 14 so that the tubular member 12 can be opened and fitted around and removed from the leg or arm. Member 12 may be viewed as having an outside joint portion 22 which fits against the outside of the joint and an inside joint portion 24 which fits along the inside of the joint. Longitudinal slit 14 is preferably provided between portions 22 and 24. Outside joint portion 22 has an opening 32 for exposing the elbow or knee for greater limb flexibility and comfort. Releasable member fasteners such as hook and loop fasteners 34 hold member 12 closed around the limb during use.

Along the inside joint portion 24 exterior surface is provided the tensioning means. The tensioning means preferably include a longitudinal elastic strip 40 connected to spaced apart connection points at either side of the joint. Strip 40 may be a rubber strip or a rubber band, and provides a range of tension, rather than a single tension because elastic resistance increases as the limb opens around the joint. The range of strip 40 stretch, and thus the range between the initial and final strip 40 tension for joint flexing, is selected to apply a desired magnitude of tension for a particular condition and stage of recovery of a particular patient. In other words the initial and final tension magnitudes and the tension levels in between are all shifted to higher or lower tension magnitudes as desired.

For one embodiment, each end of elastic strip 40 passes through a locking button 42. Each locking button 42 is preferably a metal cylinder 42a having a radial flange 42b at one end and a diametric passageway (not shown) through which the strip 40 passes and is secured. See FIG. 1. A first button hole plate 50 is secured against or into an opening in the wall of tubular member 12 over the forearm and a second button hole plate 60 is fitted against or into an opening in the wall of tubular member 12 over the upper arm, the plates 50 and 60 each including a series of button holes 44 arrayed longitudinally along tubular member 12. Each button hole 44 has a circular portion 44a sized to pass button radial flange 42b and a radially extending slot 44b sized to pass cylinder 42a but not the flange 42b. Slot 44b is directed generally toward the opposing button hole plate 50 or 60 on tubular member 12. Elastic strip 40 is engaged by fitting the flange 42b of the button 42 at one strip 40 end through a button hole 44 in first button hole plate 50 or 60 and sliding the cylinder 42a into the slot 44b so that the button 42 is locked within the hole 44, and fitting the button 42 into a button hole 44 in the opposing plate 60 or 50 in the same way. The tension in strip 40 is determined by the positions of the button holes 44 selected. The farther apart the holes 44 are, the greater the stretch of and tension in the elastic strip 40.

For another embodiment, a first rivet 72 having a broad flexible head 76 is provided in tubular member 12 over the forearm and a similar second rivet 74 is provided in tubular member 12 over the upper arm. See FIG. 2. An end of the elastic strip 40 is removably wound around first rivet 72, is stretched to a selected elastic elongation and thus to a desired tension level, and then the other end of strip 40 is removably wound around second rivet 74. Friction of the strip 40 against the flexible rivet heads 76 prevents strip 40 from unwinding until the caregiver manually unwinds strip 40. Such rivets 72 and 74 and such a strip 40 may be provided on each side of tubular member 12 for applying greater tension.

The flexible tubular member is preferably made of a relatively stiff, flexible cloth material, although construction from many materials including some plastics are contemplated. Buttons 42 and button hole plates 50 and 60 are preferably made of aluminum or a suitable plastic.

While the invention has been described, disclosed, illustrated and shown in various terms or certain embodiments or modifications which it has assumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

I claim as my invention:

1. A brace apparatus for applying tension to the fore portion and the upper portion of a human limb about a limb joint in a direction of limb closure about the joint for joint therapy, comprising:

limb fore portion engaging means;

limb upper portion engaging means;

elastic strip means interconnecting the limb fore portion and the limb upper portion for creating a range of tension levels between the limb fore portion and the limb upper portion over which the limb fore portion and the limb upper portion move relative to each other;

and means for adjusting said range of tension in said elastic strip means;

wherein said limb fore portion engaging means and said limb upper portion engaging means comprise a flexible tubular member sized to fit about the human limb at the joint, said tubular member having a tubular member inside joint portion adapted to extend over the inside of a joint, having a tubular member outside joint portion adapted to extend over the outside of a joint, and having a tubular member side portion adapted to extend over the side of a joint and interconnecting said tubular member inside joint portion and said tubular member outside joint portion;

and wherein said elastic strip means is connected to said tubular member side portion at a first point adjacent to said fore limb portion and at a second point adjacent to said upper limb portion;

such that said elastic strip means remains stretched and exerts tension substantially to the point at which the limb fore portion and the limb upper portion abut each other.

2. The apparatus of claim 1, wherein the tubular member comprises a longitudinal slit for opening said member for placement of said member about the limb;

and tubular member fastener means at said longitudinal slit releasibly fastening said slit against opening and thereby securing said member about the limb.

3. The apparatus of claim 2, wherein said means for adjusting said range of tension comprises a button secured to said strip means and a longitudinal series of button holes in said member for receiving said button, such that the range of tension in said elastic member is selected by selecting a button hole for receiving said button.

4. The apparatus of claim 2, wherein said means for adjusting said range of tension comprises rivet means connected to said member about which said elastic strip means is removably wound to hold said strip means at a selected elastic elongation.

5. The apparatus of claim 2, wherein said tubular member comprises an opening positioned to expose the outside portion of the joint.

6. A brace apparatus for applying tension to the fore portion and the upper portion of a human limb about a limb joint in a direction of limb closure about the joint for joint therapy, comprising:

limb fore portion engaging means;

limb upper portion engaging means;

elastic strip means interconnecting the limb fore portion and the limb upper portion for creating a range of tension levels between the limb fore portion and the limb upper portion over which the limb fore portion and the limb upper portion move relative to each other;

and means for adjusting said range of tension in said elastic strip means;

wherein the limb fore portion engaging means and said limb upper portion engaging means comprise:

a flexible tubular member sized to fit about the human limb at the joint, said tubular member having a longitudinal slit for opening said member for placement of said member about the limb;

and tubular member fastener means at said longitudinal slit releasibly fastening said slit against opening and thereby securing said member about the limb;

wherein said elastic strip means is connected to said member adjacent to said fore limb portion and to said member adjacent to said upper limb portion;

wherein said means for adjusting said range of tension comprises a button secured to said strip means and a longitudinal series of button holes in said member for receiving said button, such that the range of tension in said elastic member is selected by selecting a button hole for receiving said button.

7. A brace apparatus for applying tension to the fore portion and the upper portion of a human limb about a limb joint in a direction of limb closure about the joint for joint therapy, comprising:

limb fore portion engaging means;

limb upper portion engaging means;

elastic strip means interconnecting the limb fore portion and the limb upper portion for creating a range of tension levels between the limb fore portion and the limb upper portion over which the limb fore portion and the limb upper portion move relative to each other;

and means for adjusting said range of tension in said elastic strip means;

wherein the limb fore portion engaging means and said limb upper portion engaging means comprise:

a flexible tubular member sized to fit about the human limb at the joint, said tubular member having a longitudinal slit for opening said member for placement of said member about the limb;

and tubular member fastener means at said longitudinal slit releasibly fastening said slit against opening and thereby securing said member about the limb;

wherein said elastic strip means is connected to said member adjacent to said fore limb portion and to said member adjacent to said upper limb portion;

wherein said means for adjusting said range of tension comprises rivet means connected to said member about which said elastic strip means is removably wound to hold said strip means at a selected elastic elongation.

* * * * *